United States Patent [19]

Alsop

[11] Patent Number: 4,620,040

[45] Date of Patent: Oct. 28, 1986

[54] PROCESS FOR THE PREPARATION OF α-α-α-TRIFLUOROANISOLES

[75] Inventor: Derek J. Alsop, Buffalo, N.Y.

[73] Assignee: Occidental Chemical Corporation, Niagara Falls, N.Y.

[21] Appl. No.: 713,119

[22] Filed: Mar. 18, 1985

[51] Int. Cl.[4] .............................................. C07C 41/22
[52] U.S. Cl. ..................................... 568/656; 568/655
[58] Field of Search ................................ 568/655, 656

[56] References Cited

U.S. PATENT DOCUMENTS 4,436,942 3/1984 Rader et al. .......................... 570/145

FOREIGN PATENT DOCUMENTS 765527 1/1957 United Kingdom ................ 568/656

*Primary Examiner*—Bernard Helfin
*Attorney, Agent, or Firm*—James F. Tao; Arthur S. Cookfair; William G. Gosz

[57] ABSTRACT

Trifluoroanisoles of the formula

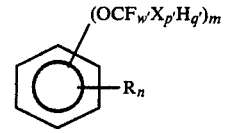

where m is 1 or 2 and n is 0 to 3, are prepared by reacting hydrogen fluoride with trichloroanisoles of the formula $$\text{(OCF}_w\text{X}_p\text{H}_q)_m\text{—C}_6\text{H}_{...}\text{—R}_n$$

in the vapor phase, in the presence of a fluorinated alumina catalyst wherein

X is halogen other than fluorine;
R is aryl, preferably 1 to 14 carbon atoms, halogen substituted aryl, halogen, alkyl of 1 to 6 carbon atoms, or alkoxy of 1 to 6 carbon atoms;
m is 1 or 2;
n is 0 to 3;
w is 0 to 2;
p is 1 to 3;
q is 0 to 2;
w+p+q is 3;
w' is 1 to 3 and is greater than w;
p' is 0 to 2 and is less than p;
q' is 0 to 2 and is equal to q; and
w'+p'+q' is 3.

12 Claims, No Drawings

PROCESS FOR THE PREPARATION OF α-α-α-TRIFLUOROANISOLES

BACKGROUND OF THE INVENTION

This invention relates to a process for the preparation of α-fluorinated anisole compounds by the catalyzed vapor phase reaction of hydrogen fluoride with an α-chlorinated anisole compound. The α-fluorinated anisoles, especially α-,α-,α-trifluoroanisoles are useful intermediates for the further preparation of various other chemical products including, for example, dyestuffs and agricultural chemicals.

Various reactions are known wherein a fluorinating agent, such as hydrogen fluoride, is reacted with an organic halide, either in the liquid or vapor phase to replace halogen atoms with fluorine atoms. Such processes may utilize atmospheric or super-atmospheric pressures and may be carried out in the presence of a catalyst. Many of the known fluorination reactions, although suitable for laboratory investigations and experiments, or small scale preparations, are unsuitable for larger scale commercial use for various reasons, such as the low purity of product obtained, low yield of the desired product, and cost of equipment employed. Moreover, a catalyst that exhibits good activity under one set of conditions, such as laboratory conditions, may be too costly for large scale preparations, or may be inefficient or inactive under different conditions.

A wide variety of fluorination catalysts are known and have been used for various fluorination processes. It is known, for example, to employ molybdenum pentachloride as a catalyst in liquid phase fluorination of benzotrichloride compounds to form benzotrifluoride compounds. (U.S. Pat. No. 4,098,832). It is further known to employ fluorinated alumina, such as fluorinated α-alumina, as a catalyst in the vapor phase fluorination of benzotrichloride compounds to form benzotrifluoride compounds. (U.S. Pat. No. 4,436,942.) However, the efficacy of a particular catalyst is highly specific and may depend on the nature of the reactants, that is, the specific compound to be fluorinated and the particular fluorinating agent employed as well as the condition of the fluorination reaction, such as temperature, pressure, and physical phase of reactants.

The preparation of α-fluorinated anisoles by reaction of hydrogen fluoride with α-chlorinated anisoles is known and is described in detail in British Pat. No. 765,527. The process disclosed is the non-catalyzed reaction of hydrogen fluoride and a α-chlorinated anisole at superatmospheric pressures and at a temperature of about 120° to about 220° Celsius. The reference discloses also that the phenol ethers are known to be sensitive and subject to splitting of the ether bridge, especially in the presence of hydrogen chloride. The patent further notes that it is surprising that ω-chlorinated (α-chlorinated) anisoles, that is to say phenol ethers containing halogen in the ω(α-)-position would withstand treatment with hydrogen fluoride, during which hydrogen chloride is evolved. In view of such disclosure it would not be expected that α-chlorinated anisoles would be capable of withstanding even more severe conditions, such as vapor phase conditions at temperatures in excess of 300° Celsius in the presence of hydrogen fluoride and evolved hydrogen chloride. The aforementioned British Pat. No. 765,527 further indicates that the antimony catalysts generally used for fluorination reactions are not beneficial and may be dispensed with.

It is an object of this invention to provide an improved process for the preparation of α-,α-,α-trifluoroanisole compounds. It is a further object to provide an improved process for the catalyzed vapor phase fluorination of α-,α-,α-trichloroanisole compounds.

SUMMARY OF THE INVENTION

In accordance with this invention, there is provided a process for the preparation of a trifluoroanisole compound of the formula

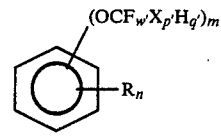

which comprises reacting hydrogen fluoride with a trichloroanisole compound of the formula

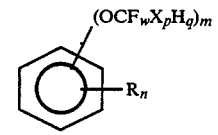

in the vapor phase in the presence of a fluorinated alumina catalyst,
wherein
X is halogen other than fluorine;
R is aryl, preferably 1 to 14 carbon atoms, halogen substituted aryl, halogen, alkyl of 1 to 6 carbon atoms, or alkoxy of 1 to 6 carbon atoms;
m is 1 or 2;
n is 0 to 3;
w is 0 to 2;
p is 1 to 3;
q is 0 to 2;
w+p+q is 3;
w' is 1 to 3 and is greater than w;
p' is 0 to 2 and is less than p;
q' is 0 to 2 and is equal to q; and
w'+p'+q' is 3.

The fluorinated alumina catalyst employed in the process of this invention may be prepared by the treatment of alumina with hydrogen fluoride. The various crystalline forms of alumina may be employed. However, it is preferred to employ the crystalline modification known as γ-alumina. The γ-alumina form is prepared by the thermal decomposition of the trihydrates of alumina or the -monohydrate. Details regarding the structure and methods of preparation of crystalline alumina, including γ-alumina are known in the literature and disclosed, for example, in Structure of Metallic Catalysts, Academic Press, 1975, pages 46–54. Gamma-alumina is commercially available in various forms, sizes and shapes. To prepare the catalysts useful in the process of this invention, it is preferred to employ as the starting material, particulate γ-alumina which may typically have a surface area of about 50 to about 800 and preferably about 50 to about 400 meters per gram and a particle size preferably in the range of about 0.2 to about 2 cm. average diameter. The pre-fluorination of the alumina is accomplished by contact with hydrogen fluoride, preferably at a temperature of about 200° to about 600° Celsius. Typically, such fluorination may be carried out by passing hydrogen fluoride, optionally in admixture with an inert diluent gas, such as nitrogen, through a column or packed bed or fluidized bed of the alumina particles. Alternatively, the fluorination may be effected in-situ in the reaction vessel prior to or during the introduction of the trichloroanisole reactant. The reaction, which is exothermic, is typically continued until the reaction exotherm ceases or substantially declines. In the preparation of the catalyst, the fluorination of the alumina will result in a decrease of surface area (as measured by standard B.E.T. nitrogen adsorption techniques). Fluorination of γ-alumina in the manner described will typically result in the formation of a fluorinated catalyst having a surface area of about 4 to about 40 square meters per gram, and a fluorine content of about 20 to about 62 weight percent.

The fluorinated alumina has been found highly effective as a catalyst for the vapor phase fluorination reaction of α-,α-, α-trichloroanisoles with hydrogen fluoride to replace the chlorine atoms of the methoxy group without substantial effect on any nuclear atoms present. In addition, it is a particular advantage that through the use of such catalyst in the process of this invention, the chloromethoxy groups of the chloroanisoles can be readily fluorinated with a high conversion to trifluoromethoxy groups.

The chloroanisoles which can be efficiently fluorinated in accordance with this invention, include those containing at least one chlorine atom in the α-position, that is on a methoxy substituent, and which may contain up to three chlorine atoms on the aromatic nucleus. Chloroanisole reactants which may be employed in the process include, for example, α,α,α-trichloroanisole; α-,α-,α-,α'-,α'-,α'-hexachloroveratrole; mono-chloro-α-,α-,α-trichloroanisole (e.g. 2-, 3-, or 4-chloro α-,α-,α-trichloroanisole); 2,4-dichloro-α-,α-,α-trichloroanisole; 2-, 4-, 6-trichloro-α,α,α-trichloroanisole and the like.

The hydrogen fluoride reactant employed in the process of this invention is anhydrous or substantially anhydrous hydrogen fluoride, for example, having a water content of less than about 2 percent.

The process of this invention is typically carried out by passing the chloroanisole vapors, together with gaseous HF, through a packed bed of particulate, fluorinated γ-alumina, preferably maintained at a temperature of about 280° to about 600° and most preferably about 300° to about 380° Celsius. Hydrogen fluoride is preferably employed in excess of the stoichiometric amount required for conversion of all the chloromethoxy groups to fluoromethoxy groups. It is preferred to employ an excess of the hydrogen fluoride of about 10% to about 200%, and more preferably about 90 to about 170% of the stoichiometric amount for the degree of fluorination desired. It is preferred to carry out the fluorination process at atmospheric pressures. However, sub-atmospheric or super-atmospheric pressures may be employed, if desired.

The flow rate or retention time of the reactants through the bed of alumina may vary considerably, depending on the volume of reactants and volume of catalyst bed. Generally, the amount of catalyst to be used is a function of the desired production rate and retention time of the process. Thus, in the present invention as related to vapor phase work, an amount of catalyst, which will give nominal retention times of from 0.5 to about 60 seconds, and preferably of from 5 to about 25 seconds, may be employed, resulting in satisfactory performance. Typically, conversions obtained with representative compounds have been as high as 98 percent and yields have been greater than 90 percent.

It is a particular advantage in the process of this invention that the fluorinated γ-alumina catalyst exhibits a high degree of physical stability and as a result may be periodically regenerated to remove carbonaceous material from the surface without substantial physical deterioration. In practice, the need for catalyst regeneration is indicated by a decrease in fluorination efficiency as evidenced by an increase in under-fluorinated substituents in the reaction product. The regeneration of the catalyst may be effected by passing air or oxygen through the catalyst bed at an elevated temperature, preferably about 200° to about 650° Celsius. The regeneration is an exothermic reaction. Substantial completion of the regeneration is indicated by a decrease in the exotherm, with a resultant lowering of temperature, caused by removal of carbonaceous material from the catalyst surface. Following such regeneration, the catalyst is again pre-fluorinated as described hereinabove, prior to use in the process of the invention.

In the above-described processes of pre-fluorination, fluorination of the organic material, and regeneration of the catalyst, it is important that the temperature of such reactions or treatments be maintained at below about 650° Celsius. At temperatures above about 650° Celsius, phase transformations of the catalyst are likely to occur, resulting in the formation of other crystalline modifications, including the formation of α-alumina type crystalline phase, which has been found to be substantially less efficient in the catalysis of the fluorination of chloroanisole compounds.

The following specific examples are provided to further illustrate this invention and the manner in which it may be carried out. It will be understood that the specific details given in the examples have been chosen for purpose of illustration and are not to be construed as a limitation of the invention. In the examples, unless otherwise indicated, all parts and percentages are by weight and all temperatures are in degrees Celsius.

EXAMPLE 1

A bed of activated alumina particles (average particle diameter about 0.25 inch) was packed in one arm of a nickel, V-shaped, tubular reactor. The reactor was heated and maintained at a temperature of about 307° to about 319° Celsius while α-,α-,α-trichloroanisole and hydrogen fluoride were fed into the reactor at rates of 0.8 parts per minute and 0.45 parts per minute respectively until 20 parts of the trichloroanisole had been introduced into the reactor. (HF was added in a stoichiometric excess of about 100%.) The reactor was then swept with a stream of nitrogen for about one hour. The reaction product was condensed in a trap immersed in an acetone/dry ice bath. The liquid reaction product was then poured onto ice. When the ice had melted, the aqueous phase was separated leaving 13.25 parts of organic product. Analysis of the organic phase by gas chromatographic techniques indicated 96.9 percent α,α,α-trifluoroanisole (an 85 percent yield).

EXAMPLE 2

The procedure of Example 1 was repeated except that the reactor temperature was maintained at 316° to 329° Celsius and the process was continued until a total of 60 parts of α-,α-,-α-trichloroanisole had been introduced into the reactor. α,α,-α-Trifluoroanisole (94 percent pure) was recovered in a 90 percent yield.

EXAMPLE 3

The procedure of Example 2 was repeated except that the reactor temperature was maintained at 310° to 328° Celsius and hydrogen fluoride was introduced at a 50 percent stoichiometric excess. α,α,α-Trifluoroanisole was recovered in a 64 percent yield.

EXAMPLE 4

The process of Example 2 was repeated except that hydrogen fluoride was added in a stoichiometric excess of about 140 percent.

EXAMPLE 5

For comparative purposes, a liquid phase fluorination employing conditions similar to those employed in a known liquid phase fluorination of benzotrichloride compounds was carried out as follows:

A mixture of 40 parts of α-,α-,α-trichloroanisole and 0.4 parts of MOCl$_5$ was heated in a reaction vessel to about 200° Celsius and hydrogen fluoride was introduced at a rate of about 0.45 parts/minute for about 30 minutes. The contents of the reaction vessel and condenser (6.4 parts) were analyzed by gas chromatographic techniques and found to contain no α-,α-,α-trifluoroanisole.

What is claimed is:

1. A process for the preparation of a trifluoroanisole compound of the formula

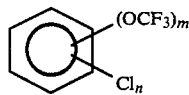

wherein m is 1 or 2 and n is 0 to 3; which comprises reacting hydrogen fluoride with a trichloroanisole compound of the formula

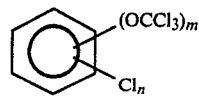

where m and n are as defined above; in the vapor phase in the presence of a fluorinated alumina catalyst.

2. A process according to claim 1 wherein the fluorinated alumina catalyst is fluorinated γ-alumina.
3. A process according to claim 1 wherein m is 1.
4. A process according to claim 1 wherein n is 1.
5. A process according to claim 1 wherein n is 0.
6. A process according to claim 1 carried out at a temperature of about 280° to about 380° Celsius.
7. A process according to claim 2 carried out at a temperature of about 280° to about 380° Celsius.
8. A process according to claim 7 wherein m is 1 and n is 1.
9. A process according to claim 7 wherein m is 1 and n is 0.
10. A process for the preparation of α-,α-,α-trifluoroanisole comprising passing a mixture of hydrogen fluoride and α-,α-,α-trichloroanisole vapors through a bed of particles of a γ-alumina catalyst maintained at a temperature of about 280° to about 600° Celsius, the hydrogen fluoride being present in an amount in excess of the stoichiometric amount required for the complete conversion of α-,α-,α-trichloroanisole to α-,α-,α-trifluoroanisole.
11. A process according to claim 10 carried out at a temperature of about 280° to about 380° Celsius.
12. A process according to claim 10 wherein the hydrogen fluoride is present in the mixture in an amount of at least about 50 percent in excess of the stoichiometric amount required.

* * * * *